US009334147B2

(12) United States Patent
Vogt et al.

(10) Patent No.: US 9,334,147 B2
(45) Date of Patent: May 10, 2016

(54) VIAL BREAKER

(75) Inventors: Sebastian Vogt, Erfurt (DE); Hubert Büchner, Nürnberg (DE)

(73) Assignee: Heraeus Medical GmbH, Wehrheim (DE)

( * ) Notice: Subject to any disclaimer, the term of this patent is extended or adjusted under 35 U.S.C. 154(b) by 972 days.

(21) Appl. No.: 13/176,364

(22) Filed: Jul. 5, 2011

(65) Prior Publication Data

US 2012/0006874 A1 Jan. 12, 2012

(30) Foreign Application Priority Data

Jul. 7, 2010 (DE) ......................... 10 2010 026 496

(51) Int. Cl.
*A61L 2/00* (2006.01)
*B67B 7/92* (2006.01)

(52) U.S. Cl.
CPC ............... *B67B 7/92* (2013.01); *Y10T 225/371* (2015.04)

(58) Field of Classification Search
CPC .................................. B67B 7/92; A61J 1/067
USPC .......................................... 422/558, 560, 562
See application file for complete search history.

(56) References Cited

U.S. PATENT DOCUMENTS

| | | | |
|---|---|---|---|
| 3,450,319 | A | 6/1969 | Ray et al. |
| 4,671,263 | A | 6/1987 | Draenert |
| 4,758,096 | A | 7/1988 | Gunnarsson |
| 4,779,763 | A | 10/1988 | Klawitter |
| 4,973,168 | A | 11/1990 | Chan |
| 5,100,241 | A | 3/1992 | Chan |
| 5,344,232 | A | 9/1994 | Nelson et al. |
| 5,551,778 | A | 9/1996 | Hauke et al. |
| 5,586,821 | A | 12/1996 | Bonitati et al. |
| 5,624,184 | A | 4/1997 | Chan |
| 5,997,544 | A | 12/1999 | Nies et al. |

(Continued)

FOREIGN PATENT DOCUMENTS

| | | |
|---|---|---|
| DE | 3640279 A1 | 6/1987 |
| DE | 19532015 A1 | 3/1997 |

(Continued)

OTHER PUBLICATIONS

Chinese Office Action for related Chinese Application No. 201110193727.2 dated Sep. 16, 2013.

(Continued)

*Primary Examiner* — Jill Warden
*Assistant Examiner* — Dwayne K Handy
(74) *Attorney, Agent, or Firm* — Norris McLaughlin & Marcus, P.A.; Christa Hildebrand

(57) ABSTRACT

The invention relates to a device for vial opening comprising an external container, in which a closed vial having a vial body and a vial head is arranged, and comprising a hollow space in the region of the vial head, whereby the hollow space comprises at least one opening and a connection to the vial, whereby the vial head, at least regions thereof, is arranged in the connection of the hollow space to the vial, and the walls of the external container comprise at least one deformable region or are altogether made of a deformable material, whereby tilting of the vial with respect to the connection is made feasible, and the diameter of the connection is adapted to the dimensions of the vial head in such a manner that the vial head can be fractured or broken off the vial body when the vial is being tilted with respect to the connection.

18 Claims, 4 Drawing Sheets

(56) References Cited

U.S. PATENT DOCUMENTS

Figure 1:
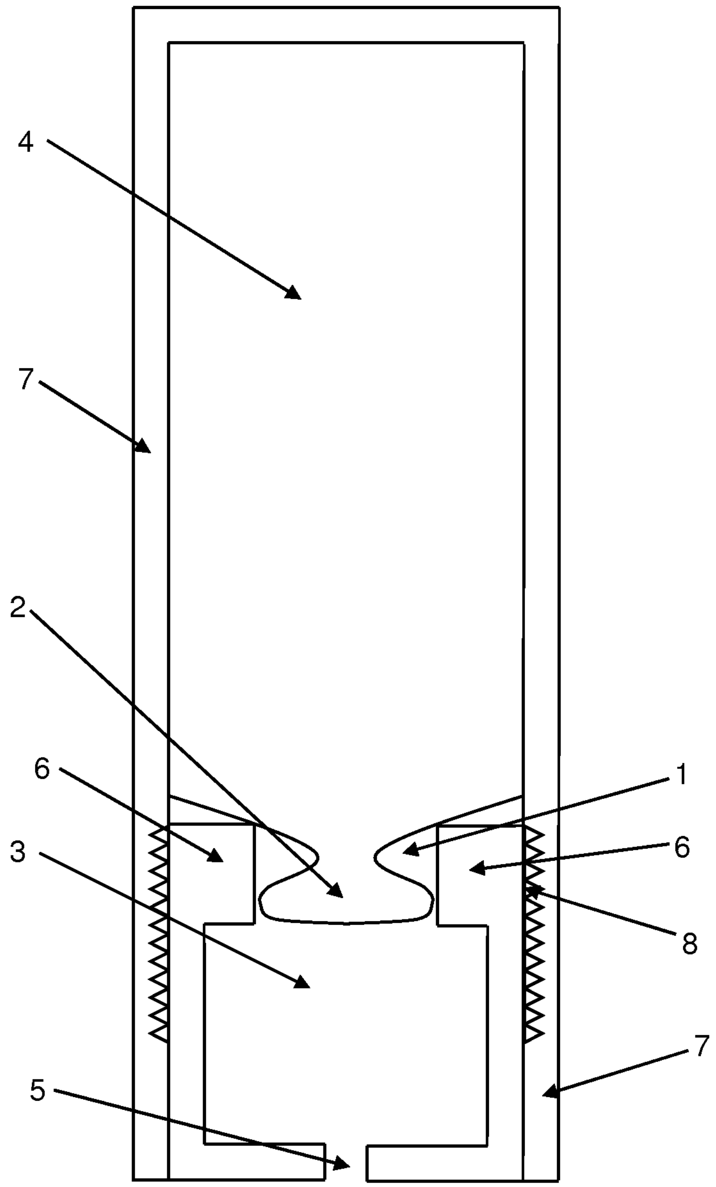

| | | | |
|---|---|---|---|
| 6,120,174 A | 9/2000 | Hoag et al. | |
| 6,257,474 B1 * | 7/2001 | Jones et al. | 225/97 |
| 6,312,149 B1 | 11/2001 | Sjovall et al. | |
| 6,709,149 B1 | 3/2004 | Tepic | |
| 6,832,703 B1 * | 12/2004 | Scott et al. | 222/189.06 |
| 2009/0152267 A1 | 6/2009 | May et al. | |
| 2011/0114212 A1 | 5/2011 | Greter et al. | |

FOREIGN PATENT DOCUMENTS

| | | | |
|---|---|---|---|
| EP | 0079983 | A1 | 6/1983 |
| EP | 0 440 354 | A1 | 8/1991 |
| EP | 0692229 | A1 | 1/1996 |
| EP | 1005901 | A2 | 6/2000 |
| EP | 1016452 | A2 | 7/2000 |
| EP | 1020167 | A2 | 7/2000 |
| EP | 1031333 | A1 | 8/2000 |
| GB | 2 081 692 | A | 2/1982 |
| JP | 3717689 | | 7/1962 |
| JP | 2011529383 | A | 12/2011 |
| WO | 94/26403 | A1 | 11/1994 |
| WO | 97/18031 | A1 | 5/1997 |
| WO | 99/67015 | A1 | 12/1999 |
| WO | 2007 042828 | A2 | 4/2007 |
| WO | 2010012114 | A1 | 2/2010 |

OTHER PUBLICATIONS

Canadian Office Action for related Canadian Application No. 2,745,126 dated Feb. 5, 2014.
Australian Office Action Report dated Aug. 31, 2012.
European Search Report of EP 11 00 4745 dated Oct. 6, 2011.
Japanese Office Action for related Japanese Application No. 2011-150979 dated Jan. 11, 2012.

* cited by examiner

VIAL BREAKER

BACKGROUND OF THE INVENTION (1) Field of the Invention

The invention relates to a device for vial opening comprising an external container, in which a closed vial having a vial body and a vial head is arranged, and comprising a hollow space in the region of the vial head, whereby the hollow space comprises at least one opening and a connection to the vial.

Accordingly, the invention provides a robust device for storing and opening monomer vials of vacuum cementing systems for polymethylmethacrylate bone cements that are pre-filled with cement powder and monomer liquid and are provided to the medical user in the form of full-prepack vacuum cementing systems.

(2) Description of Related Art

Conventional PMMA bone cements have been known for decades and are based on the ground-breaking work of Sir Charnley (Charnley, J.: Anchorage of the femoral head prosthesis of the shaft of the femur. J. Bone Joint Surg. 42 (1960) 28-30). The basic structure of PMMA bone cements has remained the same ever since. PMMA bone cements consist of a liquid monomer component and a powder component. The monomer component generally contains the monomer, methylmethacrylate, and an activator (N,N-dimethyl-p-toluidine) dissolved therein. The powder component consists of one or more polymers that are made by polymerisation, preferably suspension polymerisation, based on methylmethacrylate and co-monomers, such as styrene, methylacrylate or similar monomers, a radio-opaquer, and the initiator, dibenzoylperoxide. Mixing the powder component and the monomer component, a dough that can be shaped plastically is generated by swelling of the polymers of the powder component swell in the methylmethacrylate. Mixing the powder component and the monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Polymethylmethacrylate bone cements can be mixed by mixing the cement powder and the monomer liquid in suitable mixing beakers with the aid of spatulas. This procedure is disadvantageous in that air inclusions may be present in the cement dough thus formed and cause destabilisation of the bone cement later on. For this reason, it is preferred to mix bone cement powder and monomer liquid in vacuum mixing systems, since mixing in a vacuum removes air inclusions from the cement dough to a large extent and thus achieves optimal cement quality (Breusch S J et al.: Der Stand der Zementiertechnik in Deutschland. Z Orthop. 1999, 137: 101-07). Bone cements mixed in a vacuum have clearly reduced porosity and thus show improved mechanical properties. A large number of vacuum cementing systems has been disclosed of which the following shall be listed for exemplary purposes: U.S. Pat. No. 5,624,184, U.S. Pat. No. 4,671,263, U.S. Pat. No. 4,973,168, U.S. Pat. No. 5,100,241, WO 99/67015 A1, EP 1 020 167 A2, U.S. Pat. No. 5,586,821, EP 1 016 452 A2, DE 36 40 279 A1, WO 94/26403 A1, EP 0 692 229 A1, EP 1 005 901 A2, U.S. Pat. No. 5,344,232.

As a refinement, cementing systems have both the cement powder and the monomer liquid prepackaged in separate compartments of the mixing systems and have them mixed with each other only right before the application of the cement in the cementing system (U.S. Pat. No. 5,997,544, EP 0 692 229 A1, U.S. Pat. No. 6,709,149 B1). One issue of these systems is the transfer of the monomer liquid into the cement powder and complete mixing of these two components in order to obtain a homogeneous cement dough, which, in particular, must not contain any clusters of cement powder that has not been wetted by the monomer liquid. The Optipac™ full-prepack mixing system (Biomet Switzerland), which currently is commercially available in Europe, has simple tubes attached on the side in the lower part of the cartridge, which tubes penetrate through the cartridge wall and aspirate the monomer liquid from aluminium compound bags into the cement powder, approximately into the middle of the cement powder, through the action of a vacuum.

Aluminium compound bags have been known for packaging and storage of monomer liquid only for a few years. Very good experience in terms of the storage properties has been made with glass vials. Glass vials have been used for decades for conventional polymethylmethacrylate bone cements with good success. Aside from the perfect absence of leakage, glass vials are also advantageous in that they can be manufactured in large numbers at low prices. It is therefore reasonable to use glass vials for packaging and storage of monomer liquid in prepack vacuum cementing systems.

DE 195 32 015 A1 describes a device for mixing and dispensing multi-component products. What is proposed therein is a device for vial opening that is based on a bearing socket about which a vial holder can move in a rotating manner being provided on the outside of the cement cartridge. The head of the vial is situated on the inside of the bearing socket. Rotation of the vial holder about the bearing socket shears the vial head off the vial body. Then, the liquid from the vial can be transferred into the cartridge through an opening in the cartridge wall.

WO 97/18031 A1 proposes a device in which a vial is punctured on its bottom and the monomer liquid can subsequently flow through the hollow mixing rod into the cement cartridge.

A system for vial opening in the case of cementing systems is disclosed in EP 1 031 333 A1. In this system, a motion of the mixing rod with respect to a wedge-shaped device in the cartridge head moves the vial head transverse with respect to the vial axis, whereby the vial head is sheared off the vial body. Problems encountered in this regard include the relatively complex structure of the opening device and the risk of the wedge-shaped device getting lodged.

WO 2010/012114 A1 describes a device for opening vials. Analogous to DE 195 32 015 A1, this concerns a rotation mechanism for shearing off the vial head. The only difference from DE 195 32 015 A1 is that a rotation socket is moved with respect to the vial holder rather than the vial holder being moved with respect to the rotation socket as is the case in DE 195 32 015 A1.

The essential disadvantage of the opening devices presented in the unexamined German applications cited here is that moving mechanical parts are needed which may become lodged and whose manufacture must meet relatively high manufacturing tolerance standards in order to ensure operability.

A generic opening device is known from EP 0 079 983 A1, in which a glass vial is supported in a pressure-resistant external container and the head of the glass vial can be sheared off through the motion of a safety valve that reaches into the external container. For this purpose, the safety valve comprises an elastic sealing cuff and a pot-like lower part that reaches into the head of the vial in order to reliably shear it off. In addition, the safety valve comprises on its outlet channel means, for example a helical spring, for actuation of the safety valve.

Although the vial is very easy to open as a result of this structure, the complex structure of the safety valve including a multitude of single components is disadvantageous. This, for one, leads to increased costs in association with the manufacture of an opening device of this type, and, on the other hand, the vial may be opened inadvertently during the manufacture of said opening device.

The object of the invention is to develop a robust and simple device for storing and opening monomer vials of vacuum cementing systems for polymethylmethacrylate bone cements that are pre-filled with cement powder and monomer liquid and can be provided to the medical user in the form of prepack vacuum cementing systems. The device is to consist of a minimal number of components and be inexpensive to manufacture. Moreover, manufacture should be feasible reliably without the risk of destroying the vials. The device must be usable rapidly and safely for opening monomer vials by a user without any previous special knowledge. The device must not be associated with a risk of lodging while the vial is being opened.

BRIEF SUMMARY OF THE INVENTION

This object is met in that the vial head, at least regions thereof, is arranged in the connection of the hollow space to the vial, and the walls of the external container comprise at least one deformable region or are altogether made of a deformable material, whereby tilting of the vial with respect to the connection is made feasible, and in that the diameter of the connection is adapted to the dimensions of the vial head in such a manner that the vial head can be fractured or broken off the vial body when the vial is being tilted with respect to the connection.

For this purpose, the invention may provide the deformable region to enclose the entire circumference of the external container.

The invention can also provide the internal diameter of the connection to be equal to or larger than the external diameter of the vial head, preferably 0.5-1.5 mm larger and in particular 1 mm larger.

Another advantageous development of the invention results if the height and cross-section of the hollow space are at least of the same size as the height of the vial head up to the breaking edge of the vial.

It is also advantageous that a filter and/or sieve is arranged over the opening on the bottom of the hollow space.

Moreover, the invention can provide that the device is not deformed to a visibly recognisable extent by applying a vacuum of up to 90 mbar negative pressure.

A particularly advantageous refinement of the invention provides the external container to be attached to a hollow body, in which the hollow space is provided, whereby the hollow body comprises the opening and consists of a rigid material that cannot be deformed by hand.

In this context, the invention can provide the hollow body, which is, in particular, cylindrical, to be bordered on its top side by a vial support, in which the connection is arranged.

Moreover, the invention can provide the external container to be connected to the hollow body in a non-positive- or positive-fit type manner, in particular through a thread and/or a snap-in mechanism.

Devices according to the invention are also proposed to have the vial include a predetermined fracturing site at the connection of vial body and vial head.

It is also preferred that the external container is made of rubbery-elastic plastic material and/or that the external container, at least one region thereof, is provided to be bellows-like.

In order to further simplify the manufacture, the invention can provide that the external container, the vial and/or the connection is/are rotationally symmetrical, in particular are cylindrical.

Another, particularly simple refinement of the invention provides that the external container is a cylindrical jacket that is open on both sides, in particular shrink-down tubing, that connects the vial and the hollow body to each other in a gas-tight manner.

Moreover, the invention proposes a cartridge system comprising a device according to any one of the preceding claims and a cement cartridge that is connected to the opening through a tubing.

In this context, the invention can provide that the device and the cement cartridge are arranged on a foot part and the device is attached on said foot part in such a manner that liquid flows from the opened vial through the hollow space and the opening into the tubing in the foot part due to gravity and/or a pressure difference.

Accordingly, the invention is based on the surprising finding that a mobile external container can be utilised to open a vial that is stored therein when the vial head is fixed with respect to the motion of the external container. This is a very easy means of attaining that the vial body can be moved with respect to the vial head, whereby the vial head fractures or breaks off the vial body.

In its simplest refinement, a vial is loosely plugged by the vial head into a bracket with a cylindrical bore hole below which a hollow space of substantial size with a hole is situated. A flexible external container is slipped over the vial and the bracket and fixed in a gas-tight manner at least on the bracket. Tight fixation on the bracket is sufficient, if the flexible external container is a hollow cylinder that is closed on one side. If the external cylinder is open on both sides, like for example shrink-down tubing, tight fixation of the external container to the vial must also be provided.

The structure is particularly easy and inexpensive to implement by this means. At the same time, the operation thereof is both easy and safe. Even under difficult circumstances, such as during surgical interventions, the application is easy and feasible even by untrained auxiliary personnel.

In order to prevent the vial from being snapped and therefore opened inadvertently, the invention can provide a rigid sleeve to be arranged over the flexible region of the external shell.

Said sleeve prevents the vial from tilting and must be pulled off prior to its use.

The fixation of the vial head can be rigidly connected to a cartridge system such that a user of the cartridge system holding same in one hand can easily open the vial with the other hand by tilting the external container, or the vial, as it may be. This renders the entire cartridge system ready-for-use.

In the scope of the present invention, the hollow space shall be understood to also include a simple tubing which does not necessarily have to be large enough to take up the broken-off vial head. The transition from hollow space to opening can then no longer be discerned. The transition from the connection to the hollow-space can also be step-less. It is only important to ensure that the broken-off vial head does not completely prevent the vial content from leaking. However, a hollow space that is of sufficient size to take up the vial head or is even suitable for accommodating a rotation of the broken-off vial head inside the hollow space is particularly advantageous since the liquid content of the broken-off vial head can leak as well under these conditions and is thus available for further use.

The main purpose of the connection is to fix the vial head with respect to a tilting motion of the vial. Moreover, a fluid connection to the hollow space and/or the opening and the tubing that may be connected to it is to be established.

By means of the opening, a vacuum can be generated in the hollow space and on the inside of the external container. By this means, the vial content can also be aspirated, or to be more specific pressed, through the opening, through the higher pressure in the vial or from outside. Moreover, with the device being in a suitable position, gravity can be utilised to let the vial content flow through the connection, the hollow space, and the opening.

BRIEF DESCRIPTION OF THE SEVERAL VIEWS OF THE DRAWING(S)

Figure 2:
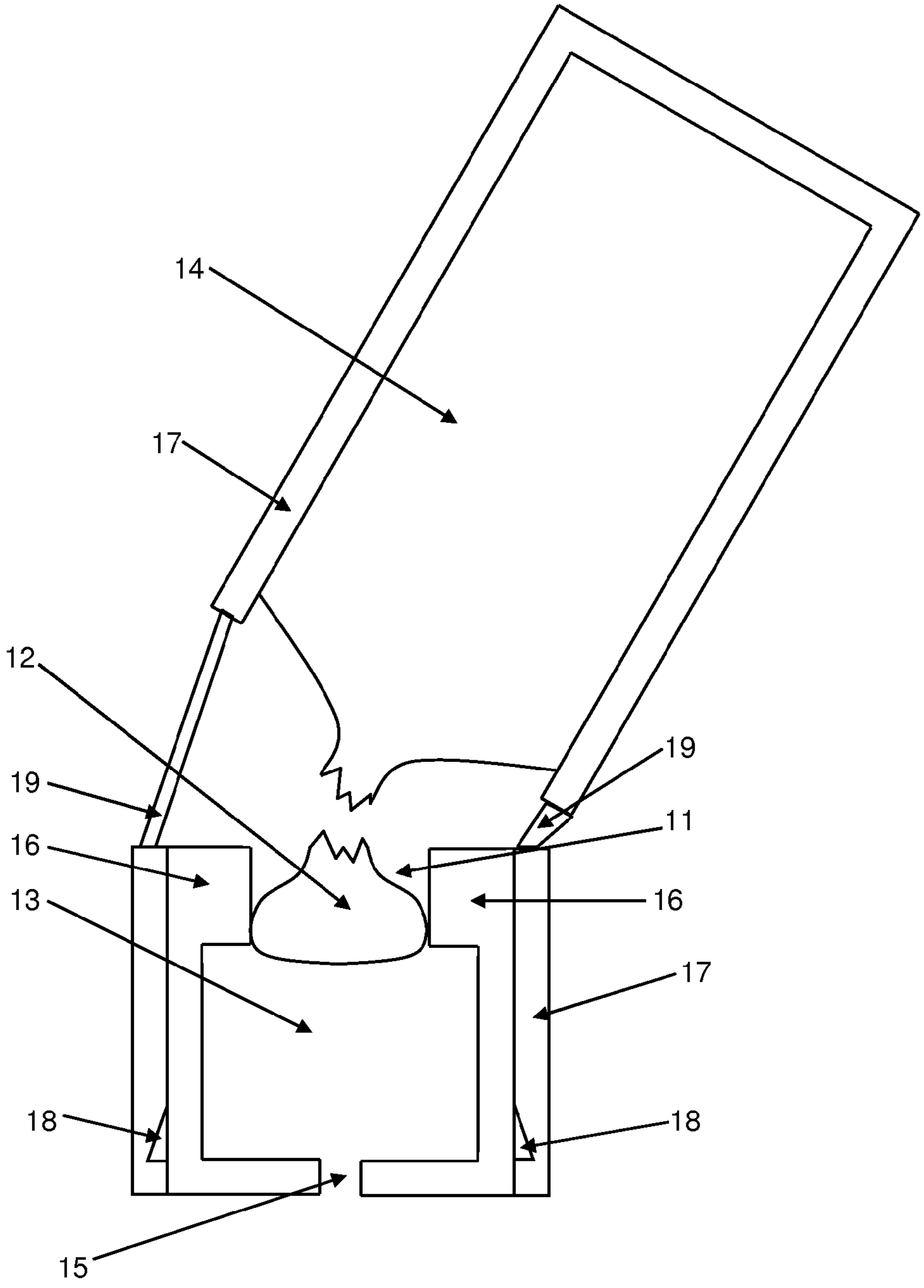
Figure 3:
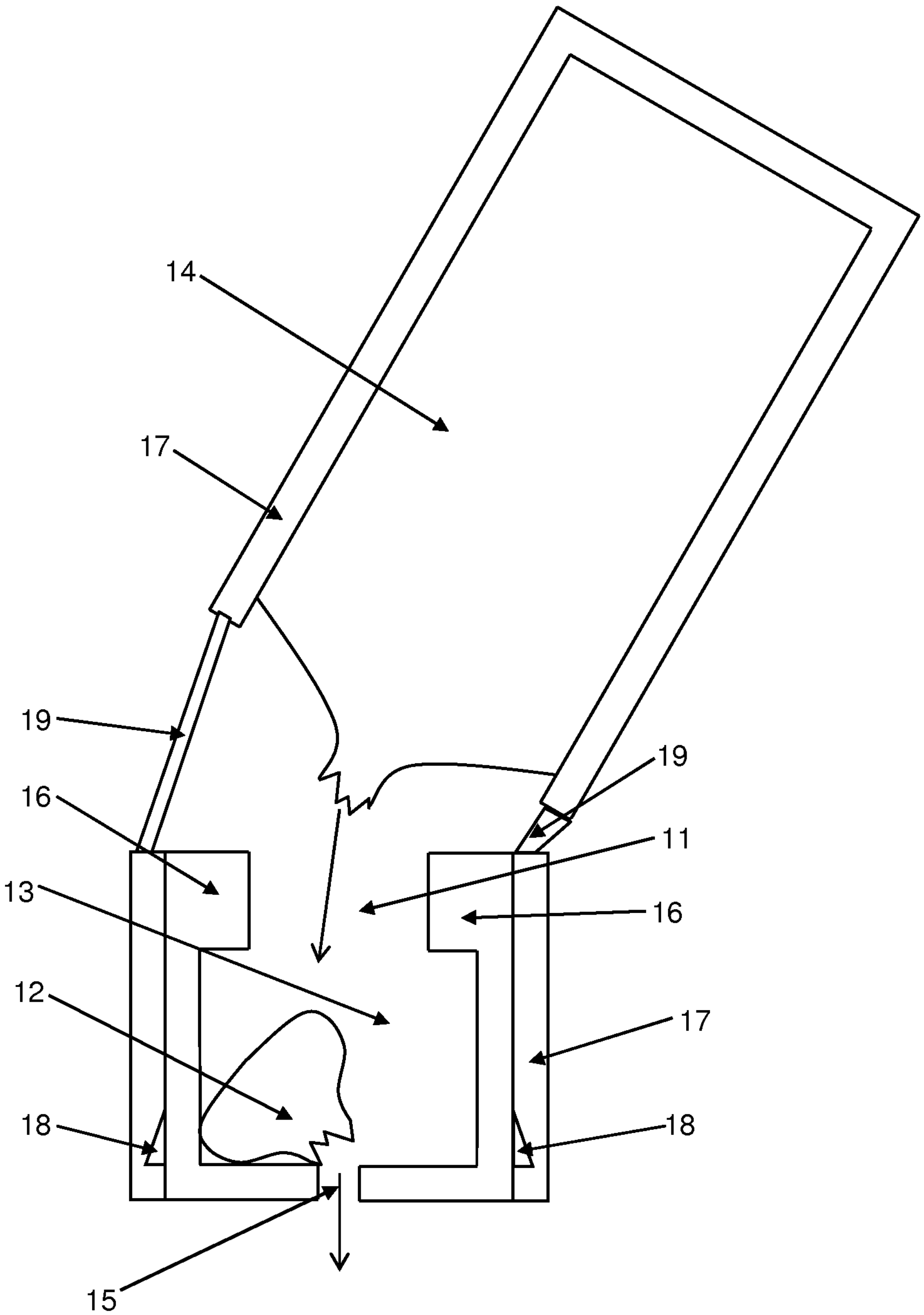
Figure 4:
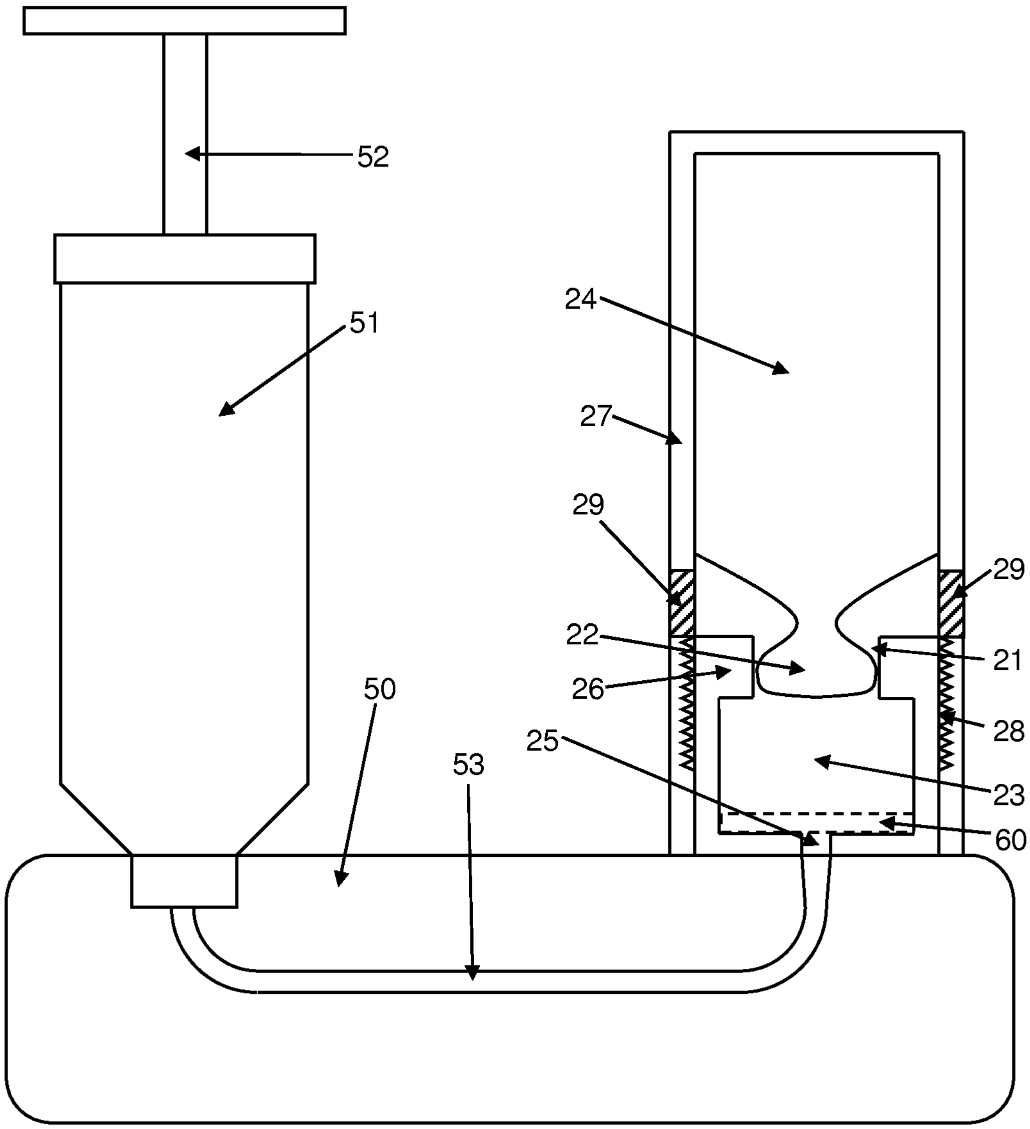

In the following, exemplary embodiments of the invention are illustrated through four schematic drawings. In the figures:

FIG. 1: shows a schematic cross-sectional view in longitudinal direction of a device ac cording to the invention with closed vial;

FIG. 2: shows a schematic cross-sectional view in longitudinal direction of an alternative device according to the invention with open vial;

FIG. 3: shows a schematic cross-sectional view of the device according to the invention according to FIG. 2 with the vial head fallen down; and FIG. 4: shows a schematic cross-sectional view of a device according to the invention in a cartridge system according to the invention.

DETAILED DESCRIPTION OF THE INVENTION

FIG. 1 shows a schematic cross-sectional view of a device according to the invention having a connection (1), in which a vial head (2) is arranged, whereby the connection (1) connects a hollow space (3) to a region, in which a vial (4) is arranged. The vial (4) can, for example, be made of glass, ceramic or any other material. An opening (5) is provided on the side of the hollow space (3) that is opposite from the connection (1). The connection (1) is, for example, a cylindrical bore hole in a vial support (6). The vial support (6) is part of a cylindrical hollow body which has the opening (5) situated in its bottom surface. An external container (7) is arranged around the vial (4) and the cylindrical hollow body. The external container (7) is connected to the cylindrical hollow body or the vial support (6), as the case may be, through a thread (8). For this purpose, an external thread (8) is provided on the cylindrical hollow body and an internal thread is provided on the external container (7).

The external container (7) is provided in the form of a cylindrical hollow body that is closed on one side and consists of a flexible material, such as, for example, rubber. In contrast, the cylindrical hollow body including the vial support (6) consists of a rigid, solid material, such as, for example, a plastic material. The vial (4) is arranged upside down in the device such that a liquid content of vial (4) leaks from the vial when the vial head (2) is broken off.

The user of said device can open the vial (4) by tilting or bending the top region of the external container (7) with respect to the vial support (6). Since the vial head (2) cannot be tilted out of said connection (1), it remains stuck in said connection (1) and ultimately breaks off or fractures altogether. For this purpose, a predetermined fracturing site can be provided on the connection of vial head (2) to vial body, in which the material from which the vial (4) is manufactured is particularly thin or carved. The broken off vial head (2) falls into the hollow space (3). Ideally, the shape and weight of the vial head (2) are such that the vial head rotates while falling off such that the content of the vial head (2) can leak from the vial head.

Simultaneously, the content of the vial (4) is also poured into the hollow space (3) since the hollow space (3) is arranged below the vial (4). Subsequently, the liquid flows from the hollow space (3) through the opening (5) and is available for use by the user.

In the present case, the purpose of the device is that the liquid contained in the vial (4) is subsequently miscible with a cement in a cement cartridge (not shown). For this purpose, the device can be firmly connected to a cartridge system (not shown).

FIG. 2 shows a schematic view of an alternative embodiment of a device according to the invention. In this device, a region (19) of an external container (17) is flexible, whereas the remainder of the external container (17) is non-flexible. A vial (14) is plugged into the upper part of the external container (17). The device shown has already been deformed through action of a force which acts from the left on the top end of the external container (17) in the figure. A vial head (12) of the vial (14) has been broken off due to the deformation. The vial head (12) was unable to follow the motion of the vial (14) since it is plugged into a connection (11) of a hollow space (13) and the upper part of the external container (17).

The connection (11) is a recess in a vial support (16), which in turn is part of a hollow body that is arranged below the vial (40). The hollow space comprises another opening (15). The external container (17) is connected to the hollow body through a snap-in mechanism (18).

In order for the vial head (12) not to break off prematurely during manufacture or transport, a rigid sleeve (not shown) can be provided to be arranged around the external container (17). Said sleeve then needs to be removed before opening the vial (14). The flexible region (19) can consist of a different material than the remainder of the external container (17) What can be provided alternatively, is that both the flexible region (19) and the external container (17) consist of the same material, whereby the thickness of the material in the flexible region (19) is less than in the walls of the external container (17) thus providing for improved deformability in the flexible region (19).

FIG. 3 shows a schematic view of the device according to FIG. 2 after the vial head (12) has fallen down into the hollow space (13). During its fall, the vial head rotated due to its shape and condition such that the content of the vial head (12) leaked from the same into the hollow space (13) and ultimately flows out of the device through the opening (15). The content of the vial (14) also leaks from same into the hollow space (13) as is indicated by the upper arrow. Subsequently, the liquid from the opened vial (14) also leaks from the hollow space (13) through the opening (15) as is indicated by the lower arrow.

The upper part of the device (external container (17) including vial body) is still situated in an oblique position. Accordingly, the flexible region (19) has undergone a plastic deformation. Just as well, the upper part may return to its original position if the flexible region (19) could be deformed elastically and the forces acted for a short period of time only (as is shown in the exemplary embodiment according to FIG. 1) and the content of the vial (14) would leak regardless. In order for the vial head (12) not to get stuck in the connection (11) in the vial support (16), the internal diameter of the connection can be somewhat larger than the external diameter of the vial head (12).

The connection having a suitable shape can help the broken-off vial head (12) to rotate in the hollow space (13) in such a manner that the content of the vial head (12) leaks. The hollow space (13) must be of sufficient size with respect to the vial head (12) to allow the vial head (12) to rotate inside the hollow space (13). For this purpose, the vial head (12) can be shaped to be pointed and elongated, unlike the vial heads shown in the figures. What can also be provided is that the vial head (12) fractures not just in one place, but in multiple places such that the content leaks from the shards of the vial head (12) into the hollow space (13).

In order to prevent the shards from exiting through the opening (15), a sieve or a filter (not shown) may be provided above the opening (15) in the hollow space (13).

FIG. 4 shows a schematic view of a device according to the invention including an unopened vial (24) that is arranged in a cartridge system according to the invention. The closed vial (24) is supported in the upper part of an external container (27) that is connected through a thread (28) to a hollow body that is arranged on a foot part (50) of the cartridge system in a fixed manner. The foot part (50) and the hollow body of the device can also be designed as a joint preform, for example made of plastic material.

A hollow space (23) is arranged in said hollow body. A vial head (22) of the vial (24) that is supported in the device in a head-first manner is arranged in a connection (21) from the hollow space (23) to the vial (24). The connection (21) extends through a vial support (26) that borders the hollow space (23) in upward direction to the vial (24). A filter (60) is arranged over an opening (25) on the bottom of the hollow space (23) in order to separate solid particles, such as, for example, shards, from the liquid content of the vial (24). The external container (27) has a flexible region (29) that extends around the entire circumference and on which the external container (27) can be deformed. By this means, it is feasible to break off the vial head (22) by tilting the upper part of the external container (27) including the body of the vial (24), or by rotating it perpendicular to the axis of symmetry of the vial (24), as the case may be.

The opening (25) is connected to a tubing (53) in the foot part (50) that connects the device according to the invention to a cement cartridge (51). The liquid from the vial (24) can be conveyed through the tubing (53) into the cement cartridge (51) aided by a vacuum. In the latter, the liquid mixes with the cement powder and the mixture can then be expelled from the cement cartridge (51) aided by a feed plunger (52), and the cement can thus be applied. The motion of the feed plunger can also be forced by applying compressed air.

The flexible region (29) can be implemented by a bellows just as well.

A device according to the invention for storing and opening monomer vials of vacuum cementing systems can therefore be characterised in that a hollow cylinder-shaped vial support (6, 16, 26) forms a connection (1, 11, 21), whose internal diameter is equal to or larger than the vial head (2, 12, 22), in that, below the vial support (6, 16, 26) and/or the connection (1, 11, 21), a hollow space (3, 13, 23) is situated whose height is at least equal to the length of the vial head (2, 12, 22) up to the breaking edge of the vial (4, 14, 24) and whose cross-section is large enough for the vial head (2, 12, 22) broken off the vial (4, 14, 24) to be able to be situated horizontally on the underside of the hollow space (3, 13, 23), in that an opening (5, 15, 25) connecting the hollow space (3, 13 23) to the cement cartridge (51) is situated on the underside of the hollow space (3, 13, 23), and in that an external container (7, 17, 27) that can be deformed elastically in longitudinal direction and is provided as a hollow cylinder with one closed side is connected to the vial support (6, 16, 26) in such a manner that the vial head (2, 12, 22) is situated in the connection (1, 11, 21) above the hollow space (3, 13, 23) in the vial support (6, 16, 26). In this context, the invention can provide that the device is not deformed to a visibly recognisable extent by applying a vacuum of up to 90 mbar.

The external container (7, 17, 27) can be deformed elastically in longitudinal direction by action of a mechanical force. This means that the closed end of the external container (7, 17, 27) facing away from the vial support (6, 16, 26) can be moved by few degrees by simply moving it perpendicular to its axis. The vial (4, 14, 24) that is present in the external container (7, 17, 27) is thus forced along during this motion. The vial head (2, 12, 22) is situated in the hollow cylinder-shaped connection (1, 11, 21) of the vial support (6, 16, 26). The vial support (6, 16, 26) is not rubbery-elastic. This means that the vial body is sheared by moving the external container (7, 17, 27) with respect to the vial head (2, 12, 22) which does not move along. The internal diameter of the hollow cylinder-shaped vial support (6, 16, 26) is larger than the vial head (2, 12, 22). The sheared off vial head (2, 12, 22) falls through the vial support (6, 16, 26) into the hollow space (3, 13, 23) and releases the connection (1, 11, 21) of the vial support (6, 16, 26) for the monomer liquid flowing after it. Said hollow space (3, 13, 23) has a height that is larger than the total length of the severed vial head (2, 12, 22). The cross-section of the hollow space (3, 13, 23) is sufficiently large for the sheared off vial head (2, 12, 22) to be able to be situated horizontally on the bottom of the hollow space (3, 13, 23). The height of the hollow space (3, 13, 23) is important in order to allow the severed vial head (2, 12, 22) to rotate while it falls through the connection (1, 11, 21) in the vial support (6, 16, 26) in such a manner that it can be situated horizontally on the bottom of the hollow space (3, 13, 23). This allows the volume of monomer liquid that is situated in the vial head (2, 12, 22) to leak. However, it needs to be noted that the cross-section of the fracturing site between the vial head (2, 12, 22) and the vial body needs to be dimensioned as a function of the surface tension of the respective monomer liquid such that it is ensured that the vial (4, 14, 24) can leak without any difficulty upon the action of gravity onto the monomer liquid. The geometry of the vial (4, 14, 24) must be adapted to the surface tension of the monomer liquid. The effluence of monomer is enabled by the opening (5, 15, 25) that is arranged in the bottom of the hollow space (3, 13, 23).

The user only needs to briefly move the end of the external container (7, 17, 27) by a few degrees perpendicular with respect to the cylinder axis to open the vial (4, 14, 24). The fracturing of the vial (4, 14, 24) can be followed easily through the bursting noise, but is also noticeable by the resistance being suddenly overcome. It is not essential, in which direction the external container (7, 17, 27) is moved perpendicular to the cylinder axis. In contrast, it is essential that a relative motion of the upper end of the external container (7, 17, 27) perpendicular to the vial axis proceeds.

Essential advantages of the device according to the invention are that no rotating or sliding mechanical parts are required, that no jamming or lodging of the device is feasible, and that no major requirements with regard to the manufacturing tolerances need to be met. Just a minimal set of parts is required. The use of the device is simplified extremely and can be done without any difficulty even by untrained users.

The external container (7, 17, 27) can have a ribbing on the inside parallel to the cylinder axis. This can provide additional shock absorption for the vial (4, 14, 24) during transport.

It is also advantageous that the vial support (6, 16, 26) cannot be deformed in a rubbery-elastic manner.

Moreover, it is advantageous that the external container (7, 17, 27) is connected to the vial support (6, 16, 26) in a non-positive and/or positive fit-type manner. The external container (7, 17, 27) can be connected to the vial support (6, 16, 26) through a simple thread (8, 28). It is feasible just as well to provide on the external container (7, 17, 27) a snap-in mechanism (18) that can be snapped onto a circumferential fin on the vial support (6, 16, 26). It is also feasible to slip the external container (7, 17, 27) over the vial support (6, 16, 26) such that fixation is effected by the restoring force of the rubbery-elastic external container (7, 17, 27).

The external container (7, 17, 27) is preferably made of rubbery-elastic plastic material. The external container (7, 17, 27) can be designed to be bellows-shaped, if applicable. The external container (7, 17, 27) can be provided to be made of rubbery-elastic material in such a manner that a sufficiently thin wall (19, 29) is present just at the level of the fracturing site of the vial (4, 14, 24), rendering the site rubbery-elastic, and that the remaining external container (7, 17, 27) has a thicker wall that cannot be deformed elastically. Accordingly, the deformable regions (19, 29) are thinner than the walls of the external container (7, 17, 27).

The scope of the invention also includes a method for vial opening that is characterised in that the external container (7, 17, 27) including the closed vial (4, 14, 24) is moved from its cylinder axis by moving the end of the external container (7, 17, 27) that is situated opposite from the vial support (6, 16, 26) in such a manner that the vial body is moved with respect to the vial head (2, 12, 22) that is situated in a fixed manner inside the vial support (6, 16, 26), whereby the vial head (2, 12, 22) is broken off the vial body.

The features of the invention disclosed in the preceding description and in the claims, figures, and exemplary embodiments, can be essential for the implementation of the various embodiments of the invention both alone and in any combination.

LIST OF REFERENCE NUMBERS

1, 11, 21 Connection
2, 12, 22 Vial head
3, 13, 23 Hollow space
4, 14, 24 Vial
5, 15, 25 Opening
6, 16, 26 Vial support
7, 17, 27 External container
8, 28 Thread
18 Snap-in mechanism
19, 29 Deformable region
50 Foot part
51 Cement cartridge
52 Feed plunger
53 Tubing
60 Filter

What is claimed:

1. A device comprising:

a closed vial including a vial body and a vial head;

an external container including walls extending from a closed top end to an opposite open bottom end; the vial being disposed within the external container;

a vial support disposed within the external container proximate its open bottom end; the vial support having walls in physical contact with the walls of the external container, a top end with an opening defined therein and an opposite bottom end with an opening defined therein substantially aligned with the open bottom end of the external container; a hollow space within the external container defined by the walls of the vial support, the top end of the vial support and the bottom end of the vial support; a connection defined by the opening in the top end of the vial support between the hollow space and a region of the external container in which at least a portion of the vial head is arranged; and the walls of the external container comprise at least one deformable region or are altogether made of a deformable material so that the vial is tiltable with respect to the connection, wherein a diameter of the connection is adapted to dimensions of the vial head such that the vial head is fracturable or broken off the vial body when the vial is tilted with respect to the connection, wherein a height of the hollow space is at least equal in size as a height of the vial head up to a breaking edge of the vial; and the hollow space has a cross-section sufficiently large so that the hollow space accommodates rotation of a broken-off vial head inside the hollow space to a position situated horizontally on the bottom side of the hollow space.

2. The device according to claim 1, wherein the deformable region extends around the entire circumference of the external container.

3. The device according to claim 1, wherein the internal diameter of the connection is by 1 mm larger than the vial head.

4. The device according to claim 1, further comprising a filter and/or sieve arranged over the opening of the hollow space.

5. The device according to claim 1, wherein a vacuum of up to 90 mbar negative pressure is applied to the open bottom end of the external container.

6. The device according to claim 1, wherein the external container is attached to the vial support including the hollow space and whereby the vial support is made of rigid material that is not deformable by hand.

7. The device according to claim 6, wherein the vial support is cylindrical on its outside from its top end extending to its bottom end.

8. The device according to claim 7, wherein the vial support is attached to the external container by one of a non-positive- or positive-fit type manner, a thread or a snap-in mechanism.

9. The device according to claim 1, wherein a common break-off area connects the vial head to the vial and wherein the common break-off area comprises a predetermined fracturing site.

10. The device according to claim 1, wherein the external container is made of rubbery-elastic plastic material.

11. The device according to claim 1, wherein the external container includes a flexible region.

12. The device according to claim 1, wherein the external container is rotationally symmetric.

13. The device according to claim 1, wherein the external container is cylindrical.

14. The device according to claim 6, wherein the external container is a cylindrical jacket that is open on both sides, connecting the vial and the vial support in a gas-tight manner.

15. The device according to claim 7, wherein the cylindrical jacket is a shrink-down tubing.

16. A cartridge system comprising a device according to claim 1 and a cement cartridge, the device and the cement cartridge are connected by a tube extending from the opening.

17. The cartridge system according to claim 16, wherein the device and the cement cartridge are arranged to a foot part and the device is attached to the foot part to facilitate a liquid flows from the opened vial through the hollow space and the opening into the tubing in the foot part due to gravity and/or a pressure difference.

18. The device according to claim 1, wherein the vial head is secured within the external container by the connection formed by the opening in the top end of the vial support without directly physical contact with any portion of the external container.

* * * * *